(12) United States Patent
Wu et al.

(10) Patent No.: US 12,409,277 B1
(45) Date of Patent: Sep. 9, 2025

(54) MEDICAMENT DELIVERY DEVICE

(71) Applicant: Genzyme Corporation, Cambridge, MA (US)

(72) Inventors: Haiming Wu, Melbourn (GB); Alexander Hee-Hanson, Melbourn (GB); William Vespa, Boston, MA (US); Cedric Delmy, Boston, MA (US); Seth Frankel, Boston, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 18/819,570

(22) Filed: Aug. 29, 2024

(51) Int. Cl.
*A61M 5/32* (2006.01)

(52) U.S. Cl.
CPC .................. *A61M 5/3204* (2013.01)

(58) Field of Classification Search
CPC ................ A61M 5/3204; A61M 5/422; A61M 2005/1585
See application file for complete search history.

(56) References Cited

U.S. PATENT DOCUMENTS

| 2002/0010423 A1* | 1/2002 | Gross | A61M 5/14248 604/170.03 |
| 2019/0030240 A1* | 1/2019 | Cabiri | A61M 5/14248 |
| 2021/0196892 A1* | 7/2021 | Dasbach | A61M 5/50 |
| 2022/0273925 A1* | 9/2022 | Zeira | A61M 5/14248 |

OTHER PUBLICATIONS

Needle-based injection systems for medical use requirements and test methods, Part 1: Needle injection systems, ISO 11608 1:2014(E), Third Edition, Switzerland, ISO, Dec. 15, 2014, pp. 1-13.

* cited by examiner

*Primary Examiner* — Rachael E Bredefeld
*Assistant Examiner* — Fatimata Sahra Diop
(74) *Attorney, Agent, or Firm* — Fish & Richardson P.C.

(57) ABSTRACT

There is provided a medicament delivery device comprising: a main body arranged to receive a medicament cartridge; a needle for delivery of medicament from the medicament cartridge; a needle cover moveable between an initial position, in which the needle cover covers the needle, and an activated position for dispensing medicament from the medicament delivery device, wherein in the activated position the needle protrudes from a distal end of the needle cover; an outer frame, moveable relative to the main body between an extended position in which the outer frame extends past a distal end of the needle, and a retracted position in which the outer frame is moved towards the main body; an attachment element comprising an adhesive region for attaching the medicament delivery device to a surface when the needle cover is in the activated position, the attachment element comprising a protective barrier covering the adhesive region.

19 Claims, 10 Drawing Sheets

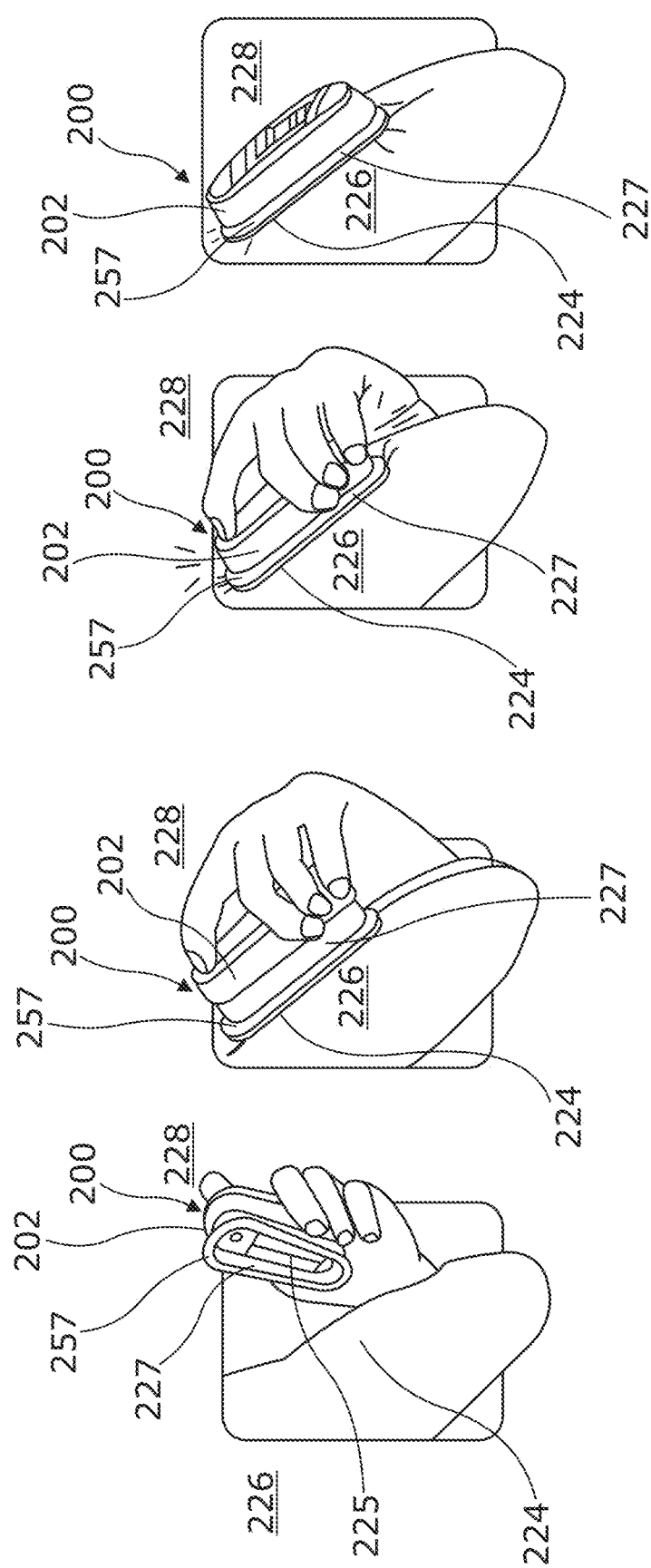

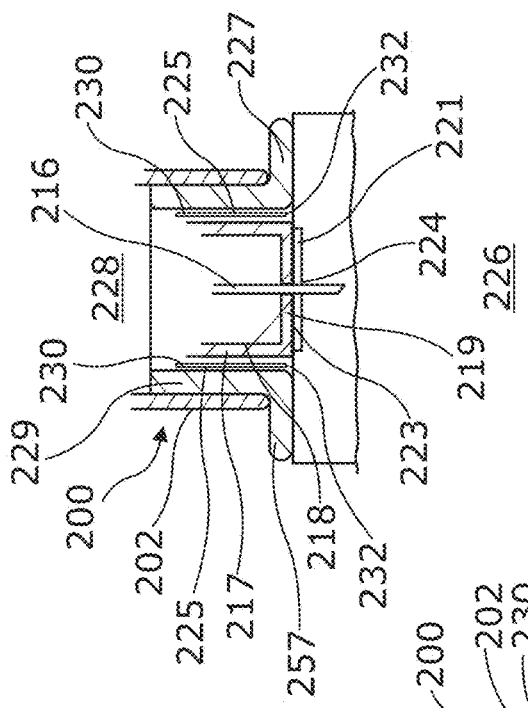
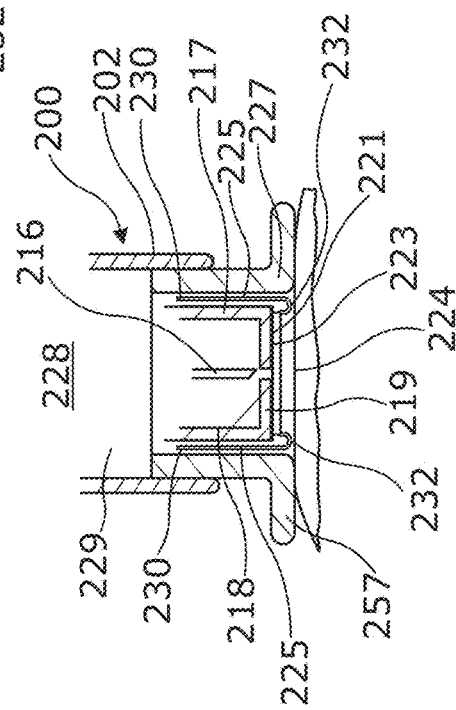
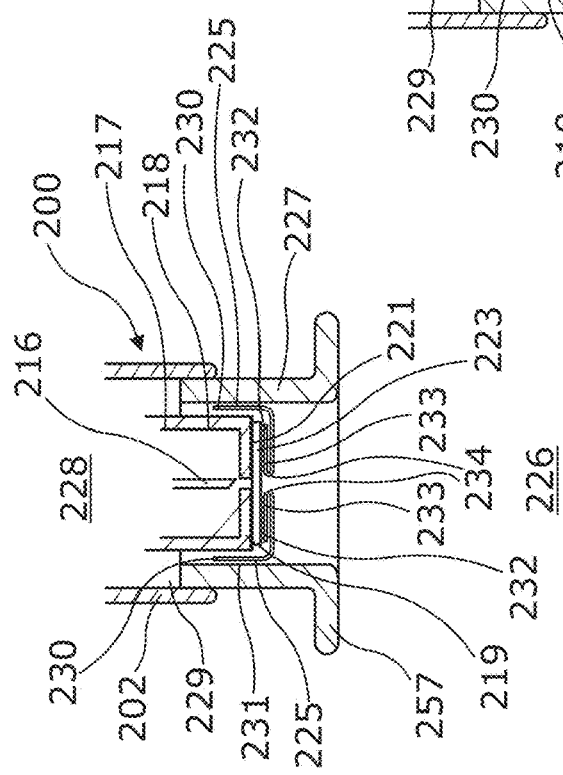

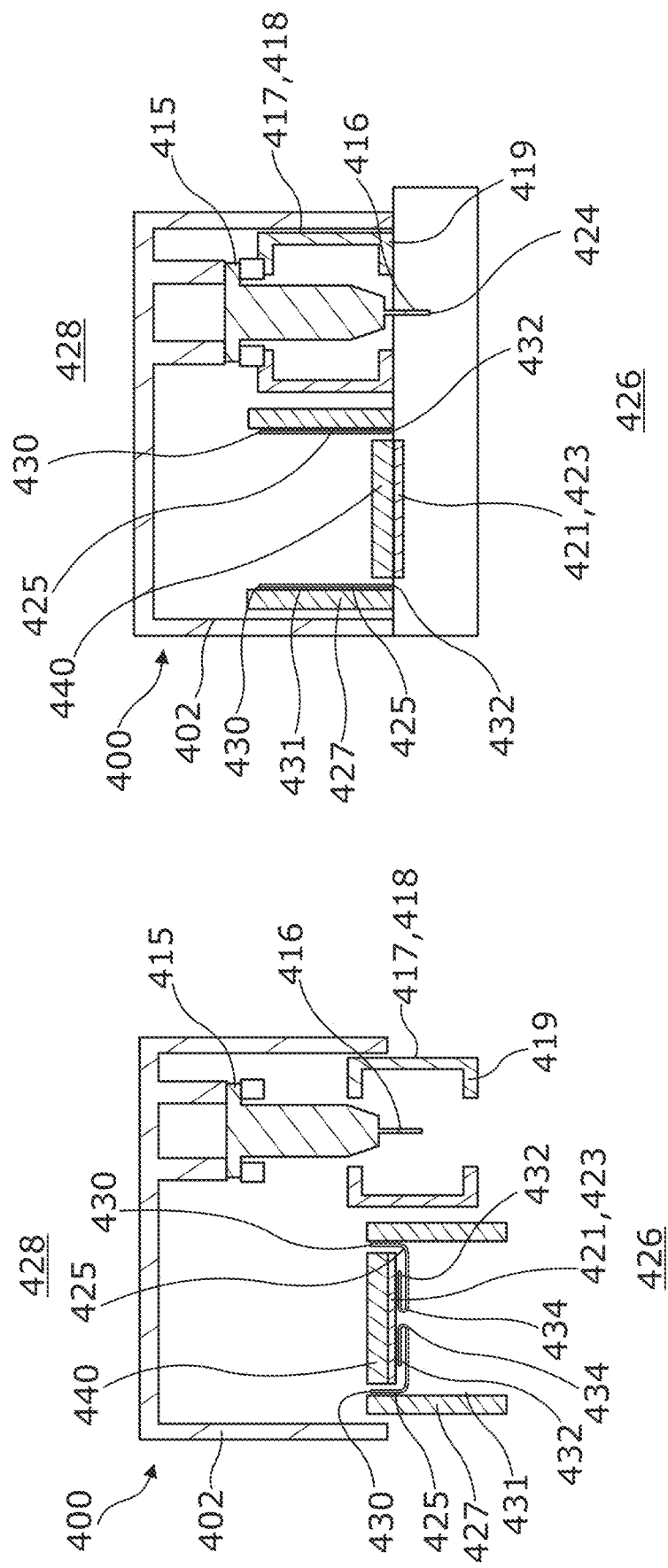

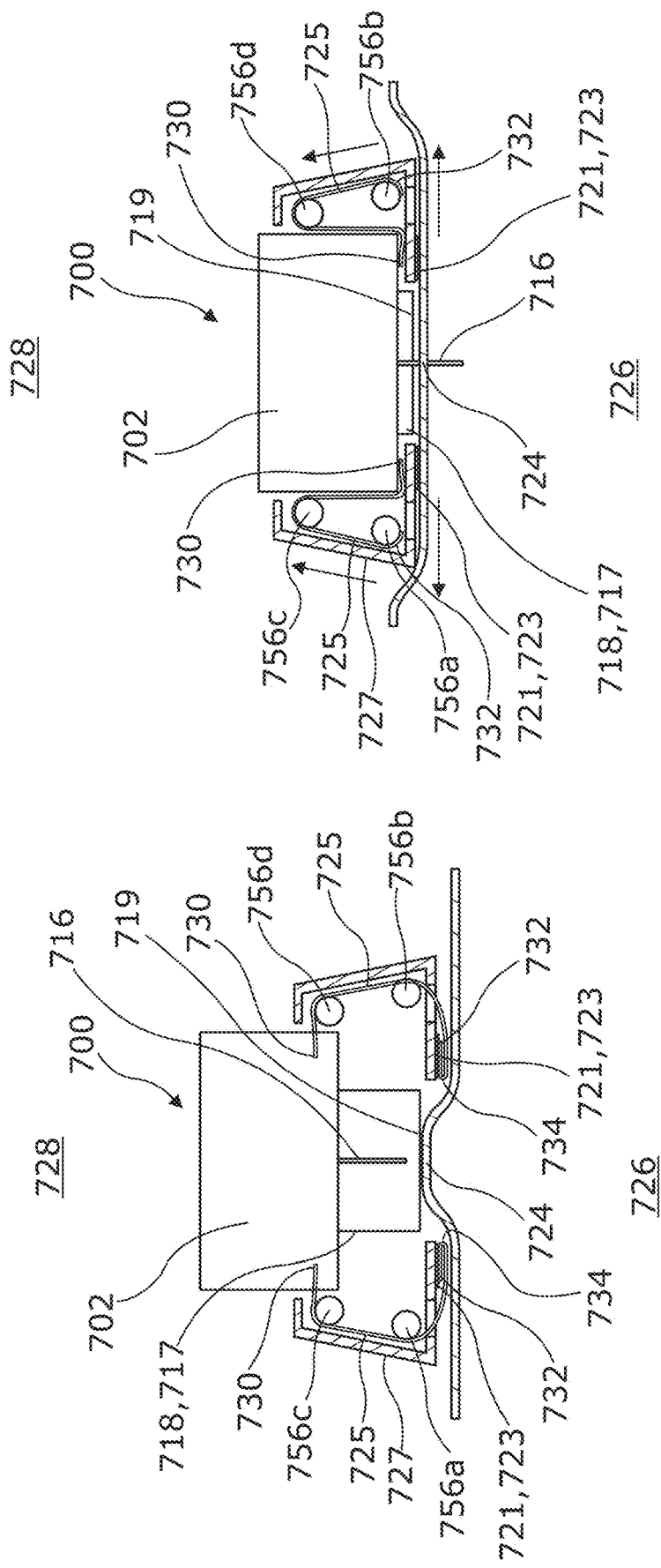

MEDICAMENT DELIVERY DEVICE

TECHNICAL FIELD

The present disclosure relates to a medicament delivery device and to a method of operating a medicament delivery device.

BACKGROUND

Medicament delivery devices are used to deliver a range of medicaments. In some devices, the device must be held in a holding position at an injection site to ensure that the correct dose of medicament is dispensed from the device, before removing the device from the injection site. It may be difficult to hold the device in the holding position whilst the medicament is dispensed. This may result in pain, discomfort, a wet injection site, early device removal and/or partial delivery of the medicament. Administering an injection is a process which presents several risks and challenges, both mental and physical. The present disclosure provides an improved medicament delivery device.

SUMMARY

A first aspect of this disclosure provides a medicament delivery device comprising: a main body arranged to receive a medicament cartridge; a needle for delivery of medicament from the medicament cartridge; a needle cover moveable between an initial position, in which the needle cover covers the needle, and an activated position for dispensing medicament from the medicament delivery device, wherein in the activated position the needle protrudes from a distal end of the needle cover; an outer frame, moveable relative to the main body between an extended position in which the outer frame extends past a distal end of the needle, and a retracted position in which the outer frame is moved towards the main body; an attachment element comprising an adhesive region for attaching the medicament delivery device to a surface when the needle cover is in the activated position, the attachment element comprising a protective barrier covering the adhesive region; wherein the protective barrier is coupled to the outer frame and is removed from the attachment element to expose the adhesive region as the outer frame is moved towards the retracted position.

The protective barrier may be removed from the attachment element, and the needle cover may be moved from the initial to the activated position, with a single action of providing a force on the medicament delivery device in a distal direction.

A first end of the protective barrier may be coupled to the outer frame, and a second end of the protective barrier may be releasably attached to the attachment element.

The protective barrier may comprise a folded portion releasably secured to the attachment element.

The folded portion may comprise a double layer of the protective barrier covering at least a portion of the attachment element.

A whole of the adhesive region may be covered by a double layer of the protective barrier.

A second end of the protective barrier may be releasably secured to the attachment element, and the second end may be folded towards the attachment element to form the folded portion.

The protective barrier may comprise a single component that extends to cover the adhesive region.

The protective barrier may comprise at least two components that extend to cover a part of the adhesive region.

The protective barrier may comprise two components that each extend to cover half of the adhesive region.

The second end may be releasably attached to a central part of the adhesive region.

The outer frame may be external to the main body in both the extended position and the retracted position.

The outer frame may be pushed inside the main body as it moves towards the retracted position.

The main body may comprise a frame cavity for receiving the outer frame in the retracted position.

The outer frame may extend around the main body in the extended, and/or the retracted position.

The outer frame may extend around the needle cover in the extended, and/or the retracted position.

The outer frame may comprise a flange on its distal most end for contacting the surface for the delivery of medicament.

Movement of the outer frame relative to the needle cover may remove the protective barrier from the attachment element.

The outer frame may be configured such that the protective barrier may be removed and the adhesive region may be adhered to the surface, before the needle cover is in the activated position.

The attachment element may be coupled to the needle cover.

The attachment element may move axially in a distal direction as the needle cover is moved towards the activated position.

An adhesive force from the attachment element may be greater than a spring force of the needle cover.

When the needle cover is in the initial position, the attachment element may be positioned set back in a proximal direction from a distal most end of the medicament delivery device.

The adhesive region of the attachment element may cover between 40% and 100% of a contact face of the needle cover or the outer frame.

The adhesive region of the attachment element may cover between 50% and 100% of the contact face of the needle cover or the outer frame.

The adhesive region of the attachment element may cover between 50% and 90% of the contact face of the needle cover or the outer frame.

The adhesive region of the attachment element may cover between 60% and 90% of the contact face of the needle cover or the outer frame.

The adhesive region may comprise one or more of an adhesive, glue or sticky tape.

The adhesive region of the attachment element may be one or more of a single patch, a plurality of patches, dots, lines or patterns of adhesive.

The attachment element may move independently of the needle cover.

The main body may comprise an attachment element support coupled to the attachment element.

The attachment element support may be fixed with respect to the rest of the main body and the attachment element may be pushed towards the surface as the main body is pushed towards the surface.

The needle may be configured to penetrate the attachment element during delivery of medicament from the medicament cartridge.

The needle may be configured to deliver medicament from the medicament cartridge without contacting the attachment element.

The outer frame may be adjacent to the needle cover.

The outer frame may be pivotable relative to the main body to move between the extended position and the retracted position.

The outer frame may comprise a pivot towards an end opposite to the needle.

The outer frame may comprise a removal arm, wherein a first end of the removal arm may be pivotally coupled to the main body, and a second end of the removal arm may be moveable relative to an internal face of a contact surface of the outer frame.

As the outer frame moves from the extended to the retracted position, the second end of the removal arm may be pushed along the internal face of the outer frame to pull the protective barrier away from the attachment element.

The first end of the removal arm may be a proximal end, and the second end of the removal arm may be a distal end.

The distal end may extend away from the main body in a distal direction towards the contact surface of the outer frame, when the outer frame is in the extended position.

The protective barrier may be pulled through an aperture in the contact surface of the outer frame.

The contact surface of the outer frame may comprise a needle hole for the needle to extend through for the delivery of medicament.

The aperture may be independent of the needle hole. For example, they are separate holes.

Alternatively, the holes may be joined.

The attachment element may comprise at least two adhesive regions, each disposed on opposite sides of the aperture.

The aperture may be in the form of a slit. The aperture may extend over the majority of a width of the contact surface.

The outer frame may extend further out from the main body at a front end than at the rear end, wherein the front end may be disposed closer to the needle than the rear end.

At the second end the removal arm may comprise a fastener to attach the removal arm to the protective barrier.

The fastener may be attached to an intermediate point of the protective barrier, between a first end and a second end of the protective barrier.

The fastener may be attached near to a mid point of the protective barrier.

The protective barrier may be removably attached to the first adhesive region, extend through the aperture in the outer frame to attach to the fastener, extend back out through the aperture and may be removably attached to the second adhesive region.

The protective barrier may comprise at least two components, each having a first end attached to the fastener, and a second end removably attached to the attachment element.

The removal arm may move towards a position parallel to the internal face of the outer frame, as the outer frame may move towards the retracted position.

As a distance between the aperture and a second end of the removal arm increases, the removal arm may pull the protective barrier away from the attachment element.

The outer frame may comprise a releasable mechanism to automatically retract the protective barrier from the attachment element, wherein the releasable mechanism may be activated as the outer frame is moved towards the main body.

The releasable mechanism may comprise at least one releasable component, and a first end of the protective barrier may be attached to the at least one releasable component, and a second end of the protective barrier may be releasably attached to the attachment element.

The releasable component may comprise a biased roller, and a first end of the protective barrier may be wound around the at least one biased roller, and a second end of the protective barrier may be releasably attached to the attachment element.

The releasable mechanism may comprise a set of releasable components.

The releasable mechanism may comprise two releasable components.

The protective barrier may comprise a number of components, equal to the number of releasable components.

The releasable mechanism may be released by a button, a lever, a latch or a catch.

The outer frame may comprise at least one tension member to hold the protective barrier in tension as it is removed from the attachment element.

The outer frame may comprise two sets of tension members, a set of distal tension members and a set of proximal tension members, wherein the protective barrier may extend around each of the distal and proximal tension members to hold the protective barrier in tension as it is removed from the attachment element.

The tension members may be rollers and may rotate as the protective barrier is removed from the attachment element.

The tension members may be stationary as the protective barrier is removed from the attachment element.

The protective barrier may drag or pull the surface in a direction away from the injection site as the protective barrier is removed from the attachment element.

Pulling the surface away from the injection site may cause a taut surface for the delivery of medicament.

The protective barrier may comprise two components and the surface may be pulled in opposing directions by each part of the protective barrier as the protective barrier is removed from the attachment element.

The adhesive regions may hold the surface taut until the device is removed from the surface.

There may be two tension members. There may be more than four tension members.

The tension member may be a static frame around which the protective barrier may be wound.

The device may be an axial form injection device.

The device may be a flat form injection device.

The device may comprise a container of medicament.

A second aspect of this disclosure provides a method of operating a medicament delivery device comprising: moving an outer frame relative to a main body of the medicament delivery device from an extended position, in which the outer frame extends past a distal end of a needle, to a retracted position, in which the outer frame is moved towards the main body; exposing an adhesive region of an attachment element by removing a protective barrier covering the adhesive region, wherein the protective barrier is coupled to an outer frame of the medicament delivery device and is removed as the outer frame is moved towards the retracted position; adhering the exposed adhesive region of the attachment element to a surface for the preparation of delivery of a medicament.

The method of operating a medicament delivery device may further comprise, moving a needle cover from an initial position, in which the needle cover may cover the needle, to an activated position for dispensing medicament from the medicament delivery device, wherein in the activated position the needle may protrude from a distal end of the needle cover.

BRIEF DESCRIPTION OF THE DRAWINGS

Embodiments will now be described, by way of example only, with reference to the accompanying drawings, in which:

FIG. 3A shows a schematic example of the medicament delivery device of FIG. 2 when an outer frame is in an extended position and a protective barrier covers an adhesive region;

FIG. 3B shows a schematic example of the medicament delivery device of FIG. 2 when an outer frame contacts an injection site;

FIG. 3C shows a schematic example of the medicament delivery device of FIG. 2 when an outer frame is moved towards a retracted position; and FIG. 3D shows a schematic example of the medicament delivery device of FIG. 2 when the medicament delivery device is adhered to an injection site;

FIG. 4A shows a schematic cross section of the medicament delivery device of FIG. 2 when an outer frame is in an extended position;

FIG. 4B shows a schematic cross section of the medicament delivery device of FIG. 2 when an outer frame is between an extended position and a retracted position;

FIG. 4C shows a schematic cross section of the medicament delivery device of FIG. 2 when an outer frame is in a retracted position;

FIG. 6A shows a schematic cross section of a medicament delivery device with an attachment element support when an outer frame is in an extended position;

FIG. 6B shows a schematic cross section of the medicament delivery device of FIG. 6A when the outer frame is in a retracted position;

FIG. 9A shows a schematic example of a medicament delivery device with an outer frame comprising two sets of tension members;

FIG. 9B shows a schematic cross section of the medicament delivery device of FIG. 9A when an outer frame is in a retracted position;

DETAILED DESCRIPTION

Figure 1:
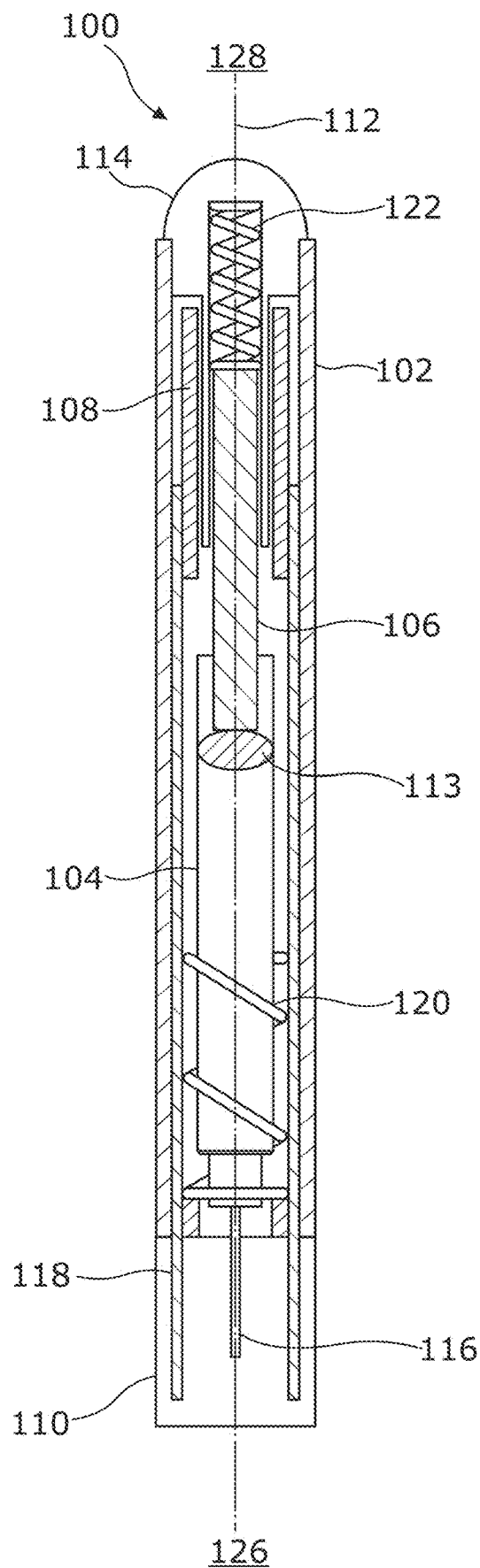
FIG. 1 shows a schematic cross section of a medicament delivery device.

A drug delivery device (also referred to as an injection device), as described herein, may be configured to inject a medicament into a subject such as a human or animal. For example, delivery could be sub-cutaneous, intra-muscular, or intravenous. Such a device could be operated by a user, who may or may not be the subject. In examples where the user is not the subject, the user may be a care-giver such as a nurse or physician. The device can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a subject's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device. The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Auto-injectors require user actions to commence medicament delivery. One of these actions may involve a user placing a needle cover (also referred to as a needle shroud or needle sleeve) against an injection site of a subject and applying an axial force to the device to cause the needle cover to retract into the housing of the device. As the needle cover retracts into the housing, the needle of the device extends beyond the needle cover and penetrates the injection site of the subject (e.g. the subject's skin). Medicament delivery may be automatically initiated in response to the retraction of the needle cover or in response to some other action by the user, for example the user pressing a button on the device. Once medicament delivery has been initiated, a medicament delivery mechanism will cause medicament contained within the device to be injected into the subject via the needle. The user should hold the device steady with respect to the injection site during the course of medicament delivery to ensure the needle remains steady within the subject. This is to minimise pain and/or discomfort for the subject, and to prevent a wet injection site, early device removal and/or partial medicament delivery.

After the device is removed from injection site, many autoinjectors cover the needle with the needle cover/needle shroud, which is extended out of the device by a control spring. During activation of the device and while holding the device steady during medicament delivery, the user must counteract the biasing force applied by the control spring to the needle cover. However, some users such as those with impaired dexterity may find it difficult to hold the device steady for a relatively long period of time during medicament delivery. It may be beneficial to provide a device which is easier to handle during medicament delivery.

Injection devices described herein use an attachment element to temporarily adhere the device to a user's skin during medicament delivery. As such, the user of the device may no longer need to counteract the biasing force of the control spring to hold the device steady against the injection site. The device may therefore be easier to handle during medicament delivery, for example by users with impaired dexterity.

Some medicament delivery devices are directly temporarily adhered to the skin, removing the need for the user to apply the hold force. However, any adhesive area will be covered, and the cover must be manually removed by a user before application of the medicament delivery device to the injection site for adhesion. Medicament delivery is then is a two handed operation starting with removal of the protective film. The protective film may also be difficult to manually remove for some people, for example by users with impaired dexterity.

FIG. 1 shows a schematic example of a cross section of an injection device 100 according to one or more aspects of the present disclosure. The injection device 100 is configured to inject a medicament into a subject. The injection device 100 comprises an outer casing 102 (also referred to as a housing or injection device body) that encloses a reservoir 104, a plunger 106 and a rotatable collar 108. The reservoir 104 typically contains the medicament to be injected, and may, for example, be in the form of a syringe. The injection device 100 can also include a cap assembly 110 that can be detachably mounted to the outer casing 102. Typically a user must remove cap 110 from the outer casing 102 before device 100 can be operated.

As shown, casing 102 is substantially cylindrical and has a substantially constant diameter along the longitudinal axis of the device 100. The injection device 100 has a distal region 126 and a proximal region 128. The term "distal" refers to a location that is relatively closer to a site of injection, and the term "proximal" refers to a location that is relatively further away from the injection site.

The outer casing 102 is closed at a proximal end by a rear casing 114. A needle 116 and a retractable needle cover 118 (also referred to as a "needle sleeve" or "needle cover") extend from a distal end of the outer casing 102. The retractable needle cover 118 is biased axially in the distal direction of the injection device 100, for example using a control spring 120. The needle cover 118 is coupled to the outer casing 102 to permit axial movement of needle cover 118 relative to the outer casing 102. For example, the cover 118 can move in a longitudinal direction parallel to longitudinal axis 112. Specifically, movement of cover 118 in a proximal direction relative to the casing 102 can cause a needle 116 to extend from distal region of the casing 102, and outside a distal end of the cover 118.

The plunger 106 is biased towards the distal end of the injection device 100 by a biasing means, for example comprising a drive spring 122. The plunger 106 is retained in an initial position by a combination of the rear casing 114 and the collar 108, preventing the biasing means from displacing the plunger 106 in the distal direction. Activation of the injection device 100 causes the collar 108 to rotate, which releases the plunger 106. Once released, the biasing means causes the plunger 106 to move in the distal direction (i.e., towards the needle 116 end of the injection device 100). The plunger 106 contacts a stopper 113 in the reservoir 104, displacing the stopper 113 in the distal direction and causing medicament stored in the reservoir 104 to be expelled from the injection device 100 via the needle 116.

Activation of the injection device 100 can occur via several mechanisms. For example, the needle 116 may be fixedly located relative to the casing 102 and initially be located within an extended needle cover 118. Proximal movement of the needle cover 118 by placing a distal end of the cover 118 against an injection site of the subject and moving the casing 102 in a distal direction will uncover the distal end of the needle 116. Such relative movement allows the distal end of the needle 116 to extend into the injection site. Such insertion is termed "manual" insertion as the needle 116 is manually inserted via the user's manual movement of the casing 102 relative to cover 118. Retraction of the cover 118 into the casing 102 causes the collar 108 to rotate, releasing the plunger 106.

Another form of activation is "automated", whereby the needle 116 moves relative to casing 102. Such insertion can be triggered by movement of the cover 118 and/or by another form of activation, such as, for example, user actuation of a button (not shown) of the injection device 100.

Typically, the user presses the needle cover 118 against an injection site to push the needle cover 118 at least partially into the device casing 102. The exposed needle 116 is pushed into the injection site of the subject. In a holding position, medicament is automatically dispensed from the needle 116 via an automated mechanism. A user must typically hold the needle cover 118 in the holding position for a predetermined period of time, to ensure that the correct dose of medicament is dispensed from the device 100, before removing the device 100 from the injection site.

The spring biasing force from the control spring 120 against which the user must apply a force to move the needle cover 118 is one component of an "activation force" of the device 100. The activation force refers to the force or force profile that the user must exert on the device 100 to move the needle cover 118 from the extended position shown in FIG. 1 to a retracted position within the casing 102 for medicament delivery. If this force or force profile is not well balanced, it can lead to difficulty in activating the device 100 for some users, or increase the pain or anxiety associated with using the device 100.

Following injection, the needle 116 can be retracted within the cover 118. Retraction can occur when the cover 118 moves distally under the biasing of the control spring 120 as a user removes the device 100 from the injection site of the subject. Once a distal end of the cover 118 has moved past a distal end of the needle 116 such that the needle 116 is covered, the cover 118 may be locked in its extended position to prevent any (substantial) proximal movement of the cover 118 relative to the casing 102 (i.e., preventing any movement of the cover 118 that would uncover the needle 116). The cover 118 may be locked by a needle cover non-return element (not shown), such as a catch.

Figure 2:
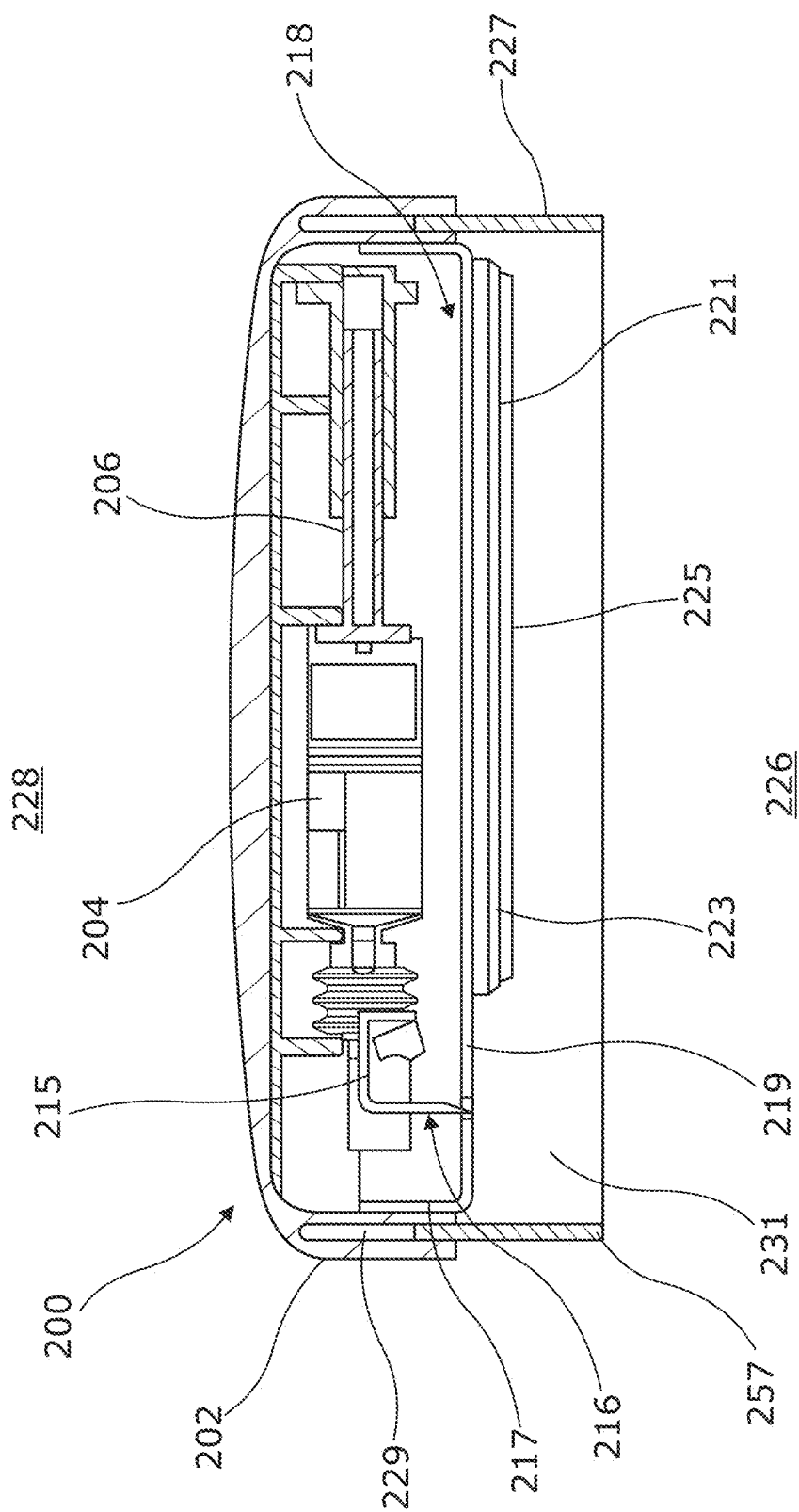
FIG. 2 shows a schematic example of a medicament delivery device in the form of a flat form injection device.

FIG. 2 shows an example of a medicament delivery device 200 in the form of a flat form injection device (hereinafter referred to as the injection device 200). In contrast FIG. 1 shows an axial form injection device. Injection device 200 is similar to the device shown in FIG. 1 (and therefore the description will not be repeated here for brevity) and similar features have been given the same reference numeral but increased by 100.

A flat form injection device can also be described as a large volume device as described above with reference to FIG. 1.

The injection device 200 has a main body 202 which is arranged to receive a medicament cartridge or container of medicament 204. The main body 202 also contains a needle carrier 215 carrying a needle 216 for the delivery of medicament to a user. The needle carrier 215 is movable with respect to the main body 202.

The injection device 200 has a needle cover 218, that is moveable between an initial position (as shown in FIG. 4A) and an activated position (as shown in FIG. 4C). In the initial position the needle cover 218 covers the needle 216. The needle cover 218 extends past the distal most end of the needle 216 to protect a user from needle sticks. In the activated position the needle 216 protrudes from a distal end of the needle cover 218. The activated position is for delivery of medicament from the injection device 200.

The needle cover 218 has a contact face 219 for contacting an injection site 224, for example a user's skin. The needle cover 218 also has needle cover side walls 217 which extend into the main body 202.

An attachment element 221 is provided on the contact face 219 of the needle cover 218. The attachment element 221 is for attaching the injection device 200 to a surface, such as a user's skin or alternative injection site 224, during delivery of medicament to the user. As the injection device 200 is directly adhered to a user's skin, the user does not need to apply a holding force for the duration of the injection. Therefore, the burden on the user to hold the needle cover 218 in a holding position for a predetermined period of time, to ensure that the correct dose of medicament is dispensed from the device 200, is reduced.

The attachment element 221 has an adhesive region 223 for releasable attachment to a surface, for example a user's skin or alternative injection site 224. The adhesive region 223 may comprise an adhesive, glue, sticky tape or any alternative known method of releasably attaching two elements. The adhesive region 223 covers between 40% and 100% of the contact face 219 of the needle cover 218. However, the precise area of coverage required by the adhesive region 223 is determined relative to the dimensions of the contact face 219, the holding force required to hold the medicament delivery device 200 during an injection, and the strength and type of adhesive used to form the releasable attachment to the surface.

The attachment element 221 is set back from a distal most end of the injection device 200, when the needle cover 218 is in the initial position. As the needle cover 218 moves towards the activated position, the attachment element 221 is moved towards the injection site 224.

The attachment element 221 has a protective barrier 225 covering the adhesive region 223. The protective barrier 225 is for protecting the adhesive region 223 from losing is adhesive properties, for example by being contaminated with dirt or debris, until the injection device 200 is ready to be attached to the injection site. The protective barrier 225 is typically a thin layer of material which can easily be removed from the adhesive region 223. Typically the protective barrier 225 is not adhesive itself, and is releasably attached to the adhesive region 223 of the attachment element 221 due to the adhesive properties of the adhesive region 223. The protective barrier 225 may be made of a thin film of polymeric material. Optionally the thickness of the protective barrier 225 is between 0.05 mm and 0.2 mm.

The injection device 200 comprises an outer frame 227. The outer frame 227 is moveable relative to the main body 202 between an extended position (as shown in FIG. 3A and FIG. 4A) in which the outer frame 227 extends past a distal end of the needle cover 218, and a retracted position (as shown in FIG. 3B and FIG. 4C) in which the outer frame 227 is received at least partially in the main body 202. In the retracted position the outer frame 227 does not extend past a distal most end of the needle cover 218. As illustrated in the embodiment shown in FIG. 2 the outer frame 227 is arranged to move axially in a proximal direction towards the main body 202 from the extended position to the retracted position as a user presses the injection device 200 against a surface.

FIG. 3A shows the injection device 200 when the outer frame 227 is in the extended position and the protective barrier 225 covers the adhesive region 223. When the outer frame 227 is in the extended position and the needle cover 218 is in the initial position, the outer frame 227 surrounds the needle cover 218. FIG. 3B shows the injection device 200, when the outer frame 227 is in the retracted position, the protective barrier 225 has been removed to expose the adhesive region 223, and the attachment element 221 is adhered to a user's skin for medicament delivery. When the outer frame 227 is in the retracted position and the needle cover 218 is in the activated position abutting an injection site 224, the outer frame 227 surrounds the needle cover 218.

FIG. 4A to FIG. 4C shows the protective barrier 225 coupled to the outer frame 227. Movement of the outer frame 227 in a proximal direction relative to the attachment element 221 removes the protective barrier 225 to expose the adhesive region 223. The protective barrier 225 is fixed at a first end 230 to an internal wall 231 of the outer frame 227. The protective barrier 225 is folded on itself to form a double layer of the protective barrier 225 at a second end 232. The second end 232, is releasably attached to the attachment element 221.

The portion of the protective barrier 225 between the second end 232 and the fold 234 can be referred to as a folded portion 233. The protective barrier 225 is folded on itself in a proximal direction, such that the folded portion 233 is located between the attachment element 221 and the rest of the protective barrier 225.

The outer frame 227 is arranged to contact the injection site 224 before the main body 202 or the needle cover 218. The outer frame 227 comprises a flange 257 on its distal most end for contacting the injection site 224 for the delivery of medicament.

As the user presses the outer frame 227 against the injection site the outer frame 227 is pushed at least partially into the main body 202. The main body 202 has a frame cavity 229 to receive the outer frame 227 within the main body 202. The frame cavity 229 extends continuously around an inside edge of the main body 202, and in the retracted position, the majority of the outer frame 227 is received within the frame cavity 229.

The outer frame 227 is moveable relative to the attachment element 221. As the outer frame 227 is pushed into the main body 202, the outer frame 227 moves the first end 230 of the protective barrier 225 in a proximal direction relative to the attachment element 221. The second end 232 of the protective barrier 225 remains substantially in the same position. This causes tension in the protective barrier 225. As the first end 230 moves further in a proximal direction, the protective barrier 225 begins to peel away from the attachment element 221. Further movement of the outer frame 227, and the first end 230, causes the protective barrier 225 to be removed at least partially from the attachment element 221. The adhesive region 223 is exposed as the protective barrier 225 is removed.

As the user continues to push the injection device 200 on to the injection site 224, the outer frame 227 moves towards its retracted position and the exposed adhesive region 223 contacts the injection site 224. As the adhesive region 223 is pressed onto the injection site 224, the injection device 200 is adhered to the user's skin. The pushing action described in this specification, can also be described as the user applying an axial force in a distal direction on the injection device 200.

Once the adhesive region 223 is adhered to the injection site, continued pushing of the injection device 200 causes the needle cover 218 to be pushed at least partially into the main body 202. In other words, the needle cover 218 is caused to move from the initial position to the activated position. As the needle cover 218 is pushed further into the main body 202, the needle 216 is inserted into the injection site 224, the plunger 206 is released and medicament delivery begins. Further details of the movement of the needle cover 218 and instigation of medicament delivery is described above with reference to FIG. 1 and is not repeated here for brevity.

Once the attachment element 221 has adhered the injection device 200 to the injection site, a user may let go of the injection device 200 until medicament delivery has been completed and in some embodiments, the needle 216 is retracted safely into the injection device 200.

A user can remove the protective barrier 225, adhere the injection device 200 to the injection site and instigate medicament delivery of the injection device, all within a single action. Typically, with a single movement in an axial distal direction. A user is also able to remove the protective barrier 225, adhere the injection device 200 to the injection site and instigate medicament delivery of the injection device with one hand. As the injection device 200 is adhered to the injection site 224, a user does not need to apply a holding force, i.e. hold the needle cover 218 in the holding position (further details of the holding position are described with reference to FIG. 1).

The adhesive force of the adhesive region 223 is stronger than the needle cover 218 spring force. If the adhesive force from the adhesive region 223 was not greater than the needle cover 218 spring force then the needle cover 218 spring force will push the injection device 200 off of the injection site 242 during medicament delivery.

Figure 5:
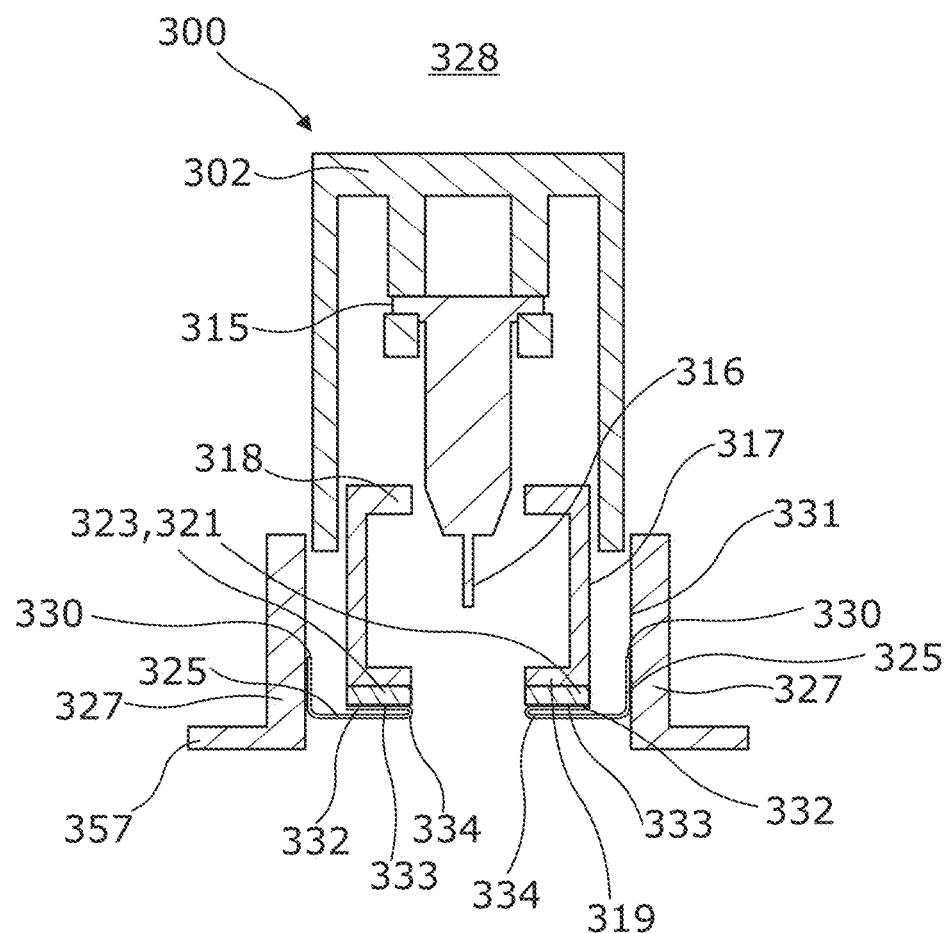
FIG. 5 shows a schematic cross section of a medicament delivery device having an outer frame positioned externally to a main body.

FIG. 5 shows an example of a medicament delivery device 300 (hereinafter referred to as the injection device 300). Injection device 300 is similar to the device shown in FIG. 2 (and therefore the description will not be repeated here for brevity) and similar features have been given the same reference numeral but increased by 100. One difference of this example is that injection device 300 comprises the outer frame 327 external to the main body 302.

FIG. 6 shows an example of a medicament delivery device 400 (hereinafter referred to as the injection device 400). Injection device 400 is similar to the device shown in FIG. 2 (and therefore the description will not be repeated here for brevity) and similar features have been given the same reference numeral but increased by 200. One difference of this example is that the attachment element 421 is not located on the contact face 419 of the needle cover 418, but on an attachment element support 440. A further difference is that the outer frame 427 is adjacent to the needle cover 418 and not surrounding the needle cover 418.

The attachment element support 440 is coupled to the main body 402 of the injection device 400. The attachment element 421 is coupled to the support 440 and is able to move independently of the needle cover 418. The attachment element support 440 is fixed with respect to the rest of the main body 402 and the attachment element 421 is pushed towards the injection site 424 as the main body 402 is pushed towards the injection site 424.

The injection device 400 is pushed towards the injection site 424 by a user. The outer frame 427 contacts the injection site 424 before the needle cover 418, and before the main body 402. The outer frame 427 is moveable relative to the main body 402 between an extended position (as shown in FIG. 6A) in which the outer frame 427 extends past a distal end of the needle cover 418, and a retracted position (as shown in FIG. 6B) in which the outer frame 427 is received at least partially in the main body 402. In the retracted position the outer frame 427 does not extend past a distal most end of the needle cover 418.

Relative motion between the outer frame 427 and the attachment element 421 removes the protective barrier 425 (as described in more detail with reference to FIG. 2). In the retracted position, the protective barrier 425 has been removed from the attachment element 440 to expose the adhesive region 423.

For an injection device with manual needle insertion, as the user continues to push the device on to the injection site 424 the needle cover 418 contacts the injection site 424. The user must overcome the needle cover spring force (as described in more detail with reference to FIG. 1) to push the adhesive region 423 against the injection site 424. The user continues to push the injection device 400 on to the injection site adhering the adhesive region 423 close to the injection site 424, and inserting the needle 416 into the injection site 424. Once the needle 416 is fully inserted the user can remove their force. As the adhesive force is stronger than the needle cover spring force medicament delivery occurs whilst the injection device 400 remains adhered to the injection site 424.

When the delivery of medicament is complete, the user then removes the injection device 400 from the injection site 424. The needle cover 418 extends out of the main body 402 under the force of the needle cover spring so that the needle 416 is not exposed.

Figures 7A, 7B:
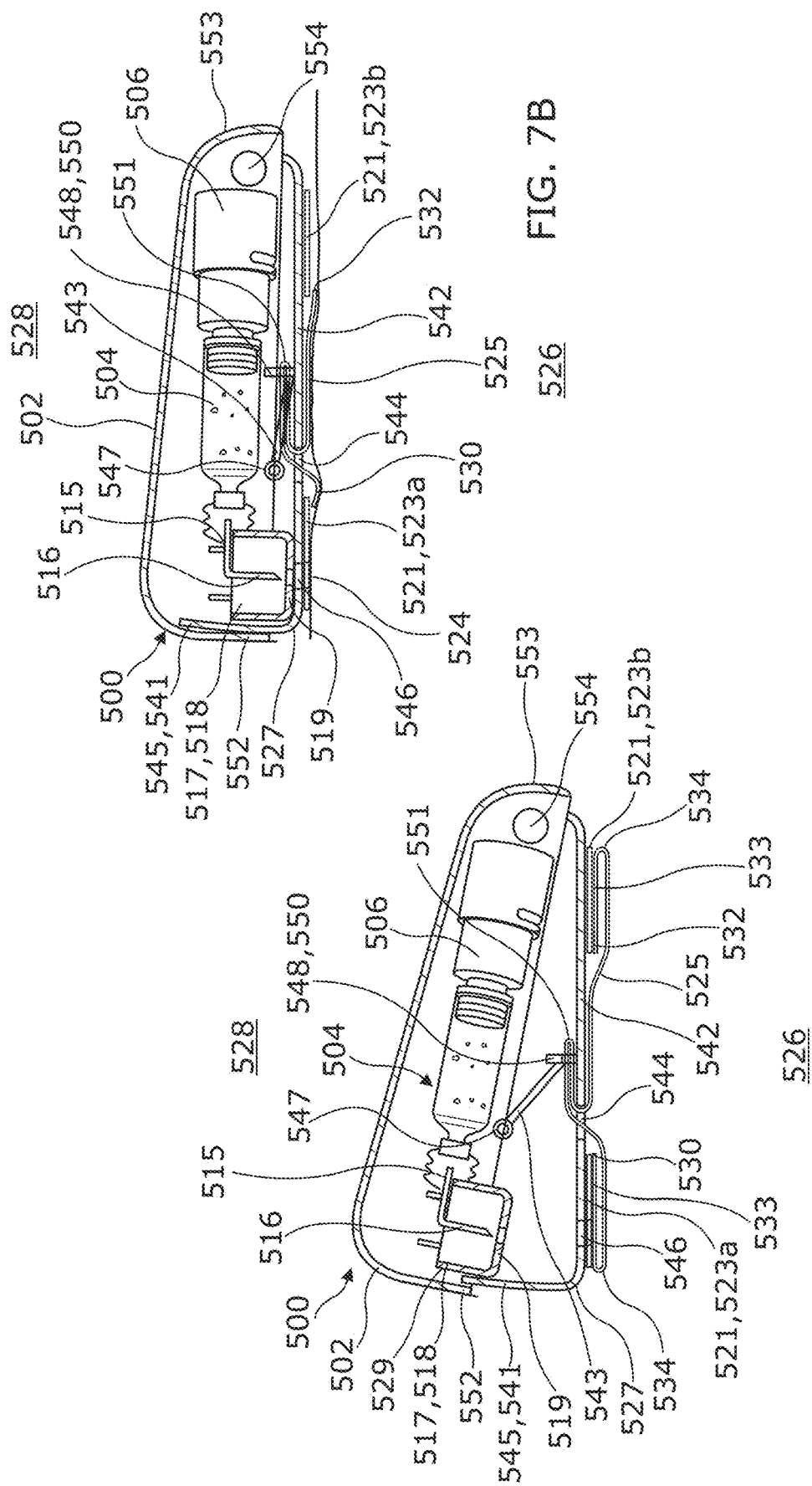
FIG. 7A shows a schematic cross section of a medicament delivery device with a pivoting outer frame in an extended position.
FIG. 7B shows a schematic cross section of the medicament delivery device of FIG. 7A with the outer frame in a retracted position.

FIG. 7A and FIG. 7B show an example of a medicament delivery device 500 (hereinafter referred to as the injection device 500). Injection device 500 is similar to the device shown in FIG. 2 (and therefore the description will not be repeated here for brevity) and similar features have been given the same reference numeral but increased by 300. One difference of this example is that the attachment element 521 is not located on the contact face 519 of the needle cover 518, but on a part of the outer frame 527. A further difference is that outer frame 527 pivots relative to the main body 502 to move between the extended and retracted position.

FIG. 7A shows the injection device 500 with the outer frame 527 in the extended position, and FIG. 7B shows the injection device 500 with the outer frame in the retracted position.

The injection device 500 comprises a front end 552 and a rear end 553. The front end 552 is closer to the needle 516 than the rear end 553. The pivotable connection 554 (referred to as a pivot from here on for brevity) between the main body 502 and the outer frame 527 is typically located towards the rear end 553. The outer frame 527 extends further out from the main body 502 at the front end 552 than at the rear end 553. This causes the outer frame 527 visible in the extended position to be wedge shaped in cross section.

The outer frame 527 has a housing 541 comprising a contact surface 542 and a surrounding wall 545 extending from the contact surface 542. The surrounding wall 545 extends at least partially into the main body 502. The surrounding wall 545 is larger at the end opposite to the pivot 554. The contact surface 542 is configured to be pushed against an injection site 524 to begin actuation of the injection device 500. The contact surface 542 comprises an aperture 544 and a needle hole 546.

Needle hole 546 is configured to be aligned with the needle 516 when the outer frame 527 is in the retracted position, such that the needle 516 can extend through the needle hole 546 for the delivery of medicament. The needle hole 546 is of a similar size to the needle such that the risk of debris and dirt entering the injection device 500 through the needle hole 546 is reduced. However, enough clearance is provided around the needle 516 such that it can easily extend and retract through the needle hole 546.

Coupled to the contact surface 542 is an attachment element 521 covered by a protective barrier 525. Some details of the attachment element 521 and protective barrier 525 have been described with reference to FIG. 2 and will not be repeated here for brevity. As shown in FIGS. 7A and 7B the attachment element 521 comprises two adhesive regions 523a, 523b. A first adhesive region 523a is disposed on one side of the aperture 544, and a second adhesive region 523b is disposed on the other side of the aperture 544. Although two adhesive regions 523a, 523b are shown in the figures, it can be appreciated that there could be more than two, or that the adhesive region could extend around the aperture 544 to form a single continuous adhesive region covering both sides of the aperture 544. The aperture 544 is of a similar width to the protective barrier 525 such that protective barrier can enter and exit the aperture without being hindered or caught by the edges of the aperture 544. Typically the aperture 544 is in the form of a slit. Typically, the aperture 544 extends over the majority of a width of the contact surface 542.

The outer frame 527 further comprises a removal arm 543. A proximal end 547 of the removal arm 543 is pivotally coupled to the main body 502. The removal arm 543 has a distal end 548 which extends away from the main body 502 in a distal direction towards the contact surface 542 of the outer frame 527, when the outer frame 527 is in the extended position.

At its distal end 548 the removal arm 543 comprises a fastener 550 to attach the removal arm 543 to the protective barrier 525. The protective barrier 525 can be attached to the fastener 550 in many known ways, for example by clamping, tying, using an adhesive, the protective barrier 525 could comprise holes and the fastener 550 could comprise pins through the holes to keep the protective barrier 525 in place. The fastener 550 is attached to an intermediate point 551 of the protective barrier 525 between its first end 530 and its second end 532. Typically, the fastener 550 is attached near to a mid point of the protective barrier 525. The protective barrier 525 covers the first adhesive region 523a, extends through the aperture 544 in the outer frame 527 to attach to the fastener 550. The protective barrier 525 then extends back out through the aperture 544 and covers the second adhesive region 523b.

Typically the protective barrier 525 is a single continuous component. However, it can be envisaged that the protective barrier 525 is more than one component attached together, either attached at the fastener 550 or to each other. For example, in the embodiment shown in FIG. 7A the protective barrier 525 may comprise two parts, a first part covering the first adhesive region 523a and a second part covering the second adhesive region 523b. The two parts may both extend through the aperture 544 to each be attached to the fastener 550.

As described with reference to FIG. 2 the protective barrier 525 may be folded at its first end to form a double layer of protective barrier 525 where it is removably attached to the attachment element. It is folded in a proximal direction to form a double layer. Differently to the embodiment described in FIG. 2, the protective barrier 525 may also be folded at its second end to form a double layer of protective barrier 525 where it is removably attached to the attachment element 521. In some embodiments the protective barrier 525 is also folded to form a double layer at the intermediate point 551, with both layers being coupled to the fastener 550.

The injection device 500 is pushed towards the injection site 524 by a user. The outer frame 527 contacts the injection site 524 before the needle cover 518, and before the main body 502. Continued force on the injection device 500 by the user causes the outer frame 527 to move from the extended to the retracted position. As the outer frame 527 moves towards the retracted position, the main body 502 applies a force in a distal direction to the removal arm 543. The distal end 548 of the removal arm 543 is moveable relative to an internal face 549 of the contact surface 542. Pushing on the removal arm 543 causes the pivot 554 to be moved in a distal direction. The removal arm 543 extends between the main body 502 and the outer frame 527. Therefore, as the distance between the main body 502 and the internal face 549 of the outer frame 527 is decreased, the removal arm 543 begins to rotate about the pivot 554, and the distal end 548 of the removal arm 543 is pushed along the internal face 549. As the removal arm 543 is pushed along the internal face 549, and the distance between the main body 502 and the internal face 549 decreases, the removal arm 543 moves towards a position parallel to the internal face 549.

The distance between the aperture 544 and the second end 548 is therefore increased as the outer frame 527 is moved towards the retracted position. The increasing distance between the aperture 544 and the second end 548 causes the removal arm 543 to pull the protective barrier 525 in through the aperture 544 and away from the attachment element 521. Removing the protective barrier 525 from the attachment element 521 exposes the adhesive regions 523a, 523b.

The user continues to push the injection device 500 on to the injection site 524 adhering the adhesive region 523a, 523b close to the injection site 524, and inserting the needle 516. Once the needle 516 is fully inserted into the injection site, the user can remove their force. Medicament delivery occurs whilst the injection device 500 remains adhered to the injection site 524. When the delivery of medicament is complete, the user removes the injection device 500 from the injection site 524 by peeling the adhesive region 523a, 523b from the injection site 524.

Figure 8B:
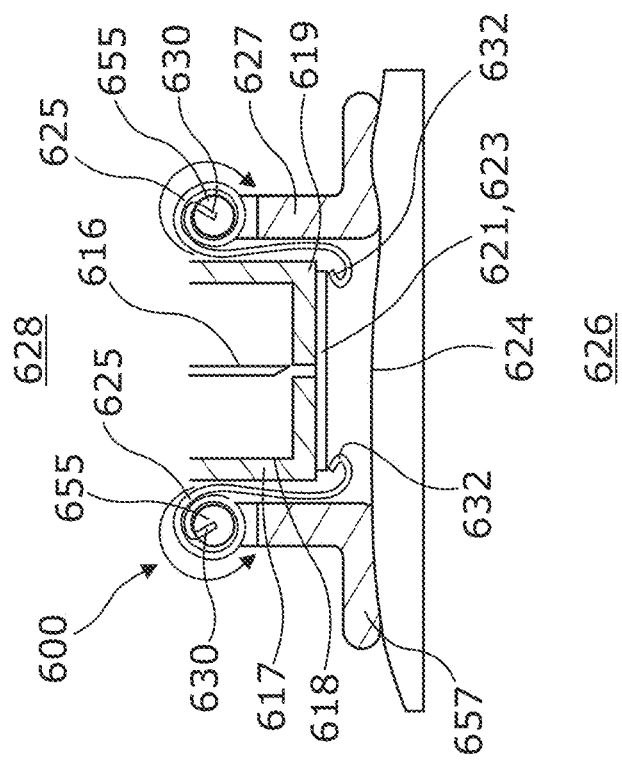
FIG. 8B shows a schematic cross section of the medicament delivery device of FIG. 8A as the outer frame moves towards a retracted position.
Figure 8A:
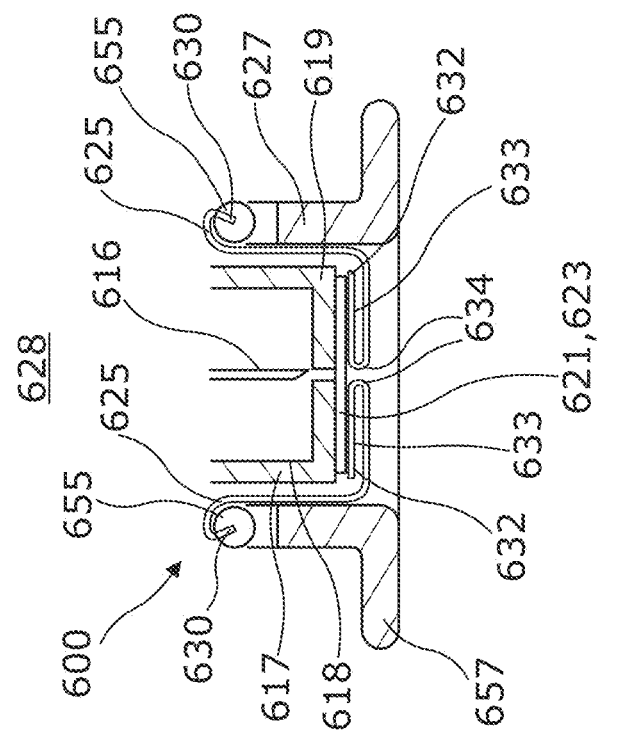
FIG. 8A shows a schematic cross section of a medicament delivery device with an outer frame comprising a releasable mechanism.

FIG. 8A and FIG. 8B show an example of a medicament delivery device 600 (hereinafter referred to as the injection device 600). Injection device 600 is similar to the device shown in FIG. 2 (and therefore the description will not be repeated here for brevity) and similar features have been given the same reference numeral but increased by 400. One difference of this example is that the outer frame 627 comprises a releasable mechanism 655 to retract the protective barrier 625.

FIG. 8A shows the injection device 600 with the outer frame 627 in the extended position, and FIG. 8B shows the injection device 600 as it moves towards the retracted position and the protective barrier 625 is removed.

The releasable mechanism 655 comprises at least one releasable component, and a first end 630 of the protective barrier 625 is attached to the at least one releasable component 655, and a second end 632 of the protective barrier 625 is releasably attached to the attachment element 621.

The releasable mechanism 655 shown in FIGS. 8A and 8B is a set of releasable components, and the releasable component is a roller. In particular a set of sprung rollers (hereinafter referred to as biased rollers). The releasable components 655 are installed towards a proximal end of the outer frame 627.

The protective barrier 625 is fixed at a first end 630 by being wound around the biased rollers 655. The protective barrier 625 is folded on itself to form a double layer of the protective barrier 625 at a second end 232. As described in more detail with respect to FIG. 2, the second end 632, is releasably attached to the attachment element 621.

The protective barrier 625 comprises a number of components or parts equal to the number of releasable components 655. As shown in FIG. 8A the protective barrier 625 comprises two parts and therefore two releasable components 655.

As the outer frame 627 is pushed against the injection site 624, the outer frame 627 moves in an axial proximal direction and releases the releasable rollers 655. The rollers 655 can be released by any known means for example a button, lever, catch or latch. Once released, the releasable rollers 655 begin to wind the protective barrier 625 around themselves, pulling the protective barrier 625 in a proximal direction. This causes tension in the protective barrier 625, which causes the protective barrier 225 to begin to peel away from the attachment element 221. Continued winding of the releasable rollers 655 causes the protective barrier 625 to be removed at least partially from the attachment element 621. The adhesive region 623 is exposed as the protective barrier 625 is removed.

As the user continues to push the injection device 600 on to the injection site 624, the outer frame 627 moves towards the retracted position and the exposed adhesive region 623 contacts the injection site 624. As the adhesive region 623 is pressed onto the injection site 624, the injection device 600 is adhered to the user's skin.

Once the adhesive region 623 is adhered to the injection site 624, a continued force on the injection device 600 in a distal direction actuates the delivery of medicament to the injection site 624. Further details of the movement of the needle cover 618 and instigation of medicament delivery is described above with reference to FIG. 1 and FIG. 2 and is not repeated here for brevity.

Once the attachment element 621 has adhered the injection device 600 to the injection site, a user may let go of the injection device 600 until medicament delivery has been completed.

FIG. 9A and FIG. 9B show an example of a medicament delivery device 700 (hereinafter referred to as the injection device 700). Injection device 700 is similar to the device shown in FIG. 2 (and therefore the description will not be repeated here for brevity) and similar features have been given the same reference numeral but increased by 500. One difference of this example is that the outer frame 727 comprises at least one tension member 756 to hold the protective barrier 725 in tension as it is removed from the attachment element 721.

The tension members 756 are two sets of rollers, a set of distal tension rollers 756a, 756b and a set of proximal tension rollers 756c, 756d. The protective barrier 725 is fixed at its first end 730 to the main body 702. The protective barrier 725 extends round the proximal tension roller 756c, 756d, then round the distal tension roller 756a, 756b. The protective barrier 725 is then coupled at its second end 732 to the attachment element 721 to cover the adhesive region 723. The protective barrier 725 is folded near to its second end 732 as described in more detail with reference to FIG. 4A to FIG. 4C. The outer frame 727 is coupled to the main body 702, and is moveable relative to the needle cover 718 and the main body 702.

As the outer frame 727 moves towards the retracted position (i.e. towards the main body 702), the protective barrier 725 is removed from the attachment element 721 to expose the adhesive region 723.

In some embodiments a taut surface at the injection site 724 may be beneficial. For example, users of the injection device 700 can have loose skin or the injection site 724 may not be a flat surface. In such cases, stretching the skin at the injection site 724 may facilitate better control of the injection site 724 relative to the device 700 in terms of stiffness, position and deformation. This may in turn increase the chances of an accurate needle insertion depth.

As the protective barrier 725 is removed from the attachment element 721, it drags across the user's skin in a direction away from the injection site 724. As the injection device 700 is pressed against the injection surface, the initial motion of the outer frame 727 relative to the main body 702 pulls the protective barrier 725 round the tension members, 756a, 756c and/or 756b, 756d to remove the protective barrier 725 from the attachment element 721. When the outer frame 727 contacts the user's skin, the attachment element 721 is held between the outer frame and the user's skin. In this position, any force on the injection device 700 in a distal direction will create a frictional force between the attachment element 721, or more specifically the adhesive region 723, and the user's skin. The frictional force can be increased or decreased by varying the axial force on the injection device 700, or changing the surface texture, for example by choice of material or by providing a textured or grippable surface. The frictional force between the protective barrier 725 and the skin causes the skin to the pulled in a direction away from the injection site 724, tightening the skin at the injection site 724. As the protective barrier 725 comprises two components in some embodiments, for example as shown in FIG. 9A and FIG. 9B, the skin is pulled in opposing directions as the protective barrier 725 is removed, facilitating a taut, flatter surface prior to the needle 716 being inserted.

Once the needle 716 has entered the injection site 724, the protective barrier 725 has dragged the skin away from the injection site 724 and the adhesive region 723 is adhered to the user's skin in the taut position. The skin is therefore held in the taut position for the duration of medicament delivery. Once medicament delivery is complete, and the injection device 700 is removed from the injection site 724, the skin returns to its original state.

In some embodiments the protective barrier 725 may be a continuous sheet that is releasably attached to the attachment element 721 at its first end 730 and at its second end 732. The protective barrier 725 extends from the attachment element 721, around the first distal tension roller 756a, around the first proximal tension roller 756c, around the second proximal tension roller 756d, around the second distal tension roller 756b, and back to the attachment element 721. The protective barrier 725 is folded on itself to form a double layer of the protective barrier 725 at both the first end 730 and the second end 732. In such embodiments, the needle 716 may penetrate the protective barrier 725 as it pierces the injection site 724.

It can be envisaged that the tension members 756 may not be rollers, but may be stationary members such as static bearings, such that the tension members 756 are stationary (and do not rotate as the rollers do) as the protective barrier 725 is removed from the attachment element 721. It can also be envisaged that there may be only two tension members 756, or more than four tension members 756. In some embodiments the tension members 756 may be replaced with a static frame around which the protective barrier 725 is wound.

Figure 10:
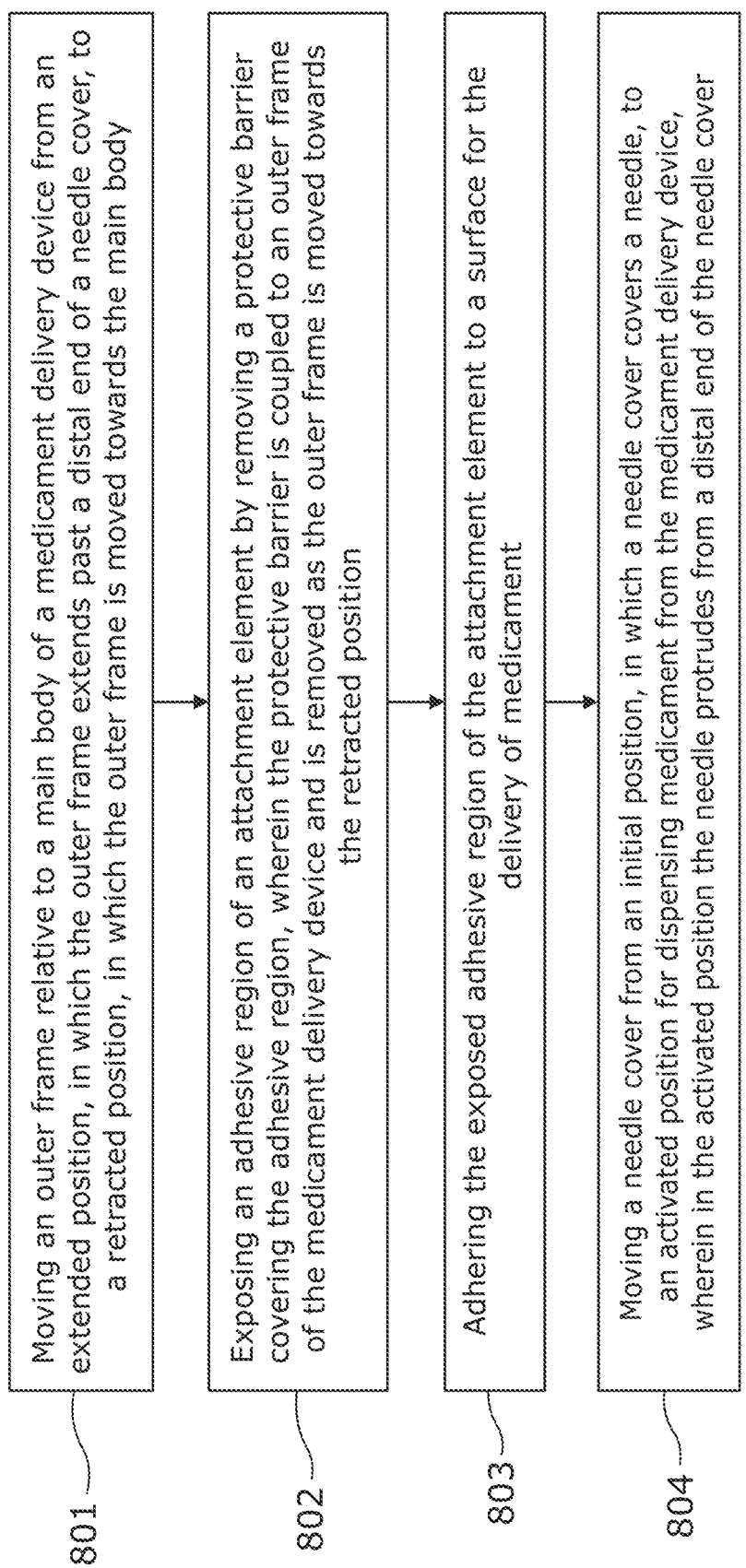
FIG. 10 shows a flow chart of an example of a method of operating a medicament delivery device.

FIG. 10 shows a flow chart of an example of a method of operating a medicament delivery device. Steps of the method illustrated in FIG. 10 may be applicable to any of the examples shown in FIG. 1 to FIG. 9.

In one step 801 the outer frame 227, 327, 427, 527, 627, 727 is moved relative to a main body 102, 202, 302, 402, 502, 602, 702 of the medicament delivery device 100, 200, 300, 400, 500, 600, 700 from an extended position, in which the outer frame 227, 327, 427, 527, 627, 727 extends past a distal end of a needle cover 118, 218, 318, 418, 518, 618, 718, to a retracted position, in which the outer frame 227, 327, 427, 527, 627, 727 is moved towards the main body 102, 202, 302, 402, 502, 602, 702.

In another step 802 the adhesive region 223, 323, 423, 523a, 523b, 623, 723 of an attachment element 221, 321, 421, 521, 621, 721 is exposed by removing a protective barrier 225, 325, 425, 525, 625, 725 covering the adhesive region 223, 323, 423, 523a, 523b, 623, 723, wherein the protective barrier 225, 325, 425, 525, 625, 725 is coupled to an outer frame 227, 327, 427, 527, 627, 727 of the medicament delivery device 100, 200, 300, 400, 500, 600, 700 and is removed as the outer frame 227, 327, 427, 527, 627, 727 is moved towards the retracted position.

In another step 803 the exposed adhesive region 223, 323, 423, 523a, 523b, 623, 723 of the attachment element 221, 321, 421, 521, 621, 721 is adhered to an injection surface 224, 324, 424, 524, 624, 724 for the delivery of medicament.

In another optional step 804 the needle cover 118, 218, 318, 418, 518, 618, 718 is moved from an initial position, in which a needle cover 118, 218, 318, 418, 518, 618, 718 covers a needle 116, 216, 316, 416, 516, 716, to an activated position for dispensing medicament from the medicament delivery device 100, 200, 300, 400, 500, 600, 700, wherein in the activated position the needle 116, 216, 316, 416, 516, 716, protrudes from a distal end of the needle cover 118, 218, 318, 418, 518, 618, 718.

In the above-described embodiments the adhesive region 223 of the attachment element 221 covers between 40% and 100% of the contact face 219. However, in alternative embodiments intended within the scope of the present disclosure, the adhesive region 223 of the attachment element 221 covers between 50% and 100% of the contact face 219. It can also be envisaged that the adhesive region 223 covers between 50% and 90% of the contact face 219, or between 60% and 90% of the contact face 219. The precise area of coverage required by the adhesive region 223 is determined relative to the dimensions of the contact face 219 and or outer frame 227, the holding force required to hold the medicament delivery device, 100, 200, 300, 400, 500, and the strength and type of adhesive used to form the releasable attachment to the surface.

In the above-described embodiments the adhesive region 223, 323, 423, 523a, 523b, 623, 723 of the attachment element 221, 321, 421, 521, 621, 721 is described as single element 223, 323, 423, 623, or two elements 523a, 523b. However, in alternative embodiments intended within the scope of the present disclosure, the adhesive region of the attachment element can be a single continuous patch (where two or more have been described), a number of patches, dots, lines or patterns of adhesive, or any combination of the above.

In the above-described embodiments the protective barrier 225, 325, 425, 525, 625, 725 is described as being a single element or two elements. However, in alternative embodiments intended within the scope of the present disclosure, any of the above described embodiments may comprise a protective barrier 225, 325, 425, 525, 625, 725 with one or more components. In embodiments where more than one component is described, it is intended within the scope of the present disclosure that the protective barrier 225, 325, 425, 525, 625, 725 may comprise a single component that extends to cover the or all adhesive regions 223, 323, 423, 523a, 523b, 623, 723.

In the above-described embodiments the protective barrier 225, 325, 425, 525, 625, 725 is not adhesive itself, and is releasably attached to the adhesive region 223, 323, 423, 523a, 523b, 623, 723 of the attachment element 221, 321, 421, 521, 621, 721 due to the adhesive properties of the adhesive region 223. However, in alternative embodiments intended within the scope of the present disclosure, the protective barrier 225 may be adhesive, for example in embodiments in which the protective barrier is attached to a part of the attachment element not covered by the adhesive region 223, or attached to a further part of the injection device 200.

In the above-described embodiments the protective barrier 225, 325, 425, 525, 625, 725 is folded on itself to form a double layer of the protective barrier 225, 325, 425, 525, 625, 725 at a second end 232, 332, 432, 532, 632, 732. This provides improved peeling of the protective barrier 225, 325, 425, 525, 625, 725 from the attachment element 221, 321, 421, 521, 621, 721. However, in alternative embodiments intended within the scope of the present disclosure, the protective barrier 225, 325, 425, 525, 625, 725 may not be folded at the second end 232, 332, 432, 532, 632, 732.

In some embodiments the needle 116, 216, 316, 416, 516, 616, 716 is configured to penetrate the attachment element 221, 321, 421, 521, 621, 721 and/or the adhesive region 223, 323, 423, 523a, 523b, 623, 723 during delivery of medicament from the medicament cartridge 104, 204, 304, 404, 504, 604, 704. In other embodiments the needle 116, 216, 316, 416, 516, 616, 716 is configured to deliver medicament from the medicament cartridge 104, 204, 304, 404, 504, 604, 704 without contacting the attachment element 221, 321, 421, 521, 621, 721 and/or the adhesive region 223, 323, 423, 523, 623, 723.

In some of the above-described embodiments the outer frame 227, 327, 427, 627, 727 comprises a flange 257, 357, 657. However, it is intended within the scope of the present disclosure that all of the injection devices 100, 200, 300, 400, 500, 600, 700 may or may not comprise a flange 257, 357, 657, for contacting the injection site 124, 224, 324, 424, 524, 624, 724.

In some of the above-described embodiments the attachment element 221, 321, 421, 521, 621, 721 is described as being set back in a proximal direction from a distal most end of the injection device 100, 200, 300, 400, 500, 600, 700. However, it is intended within the scope of the present disclosure that all of the injection devices 100, 200, 300, 400, 500, 600, 700 may comprise the attachment element 221, 321, 421, 521, 621, 721 set back in a proximal direction from a distal most end of the injection device 100, 200, 300, 400, 600, 700. For example with reference to the embodiment shown in FIGS. 7A and 7B, the outer frame 527 may comprise a rim which extends past the contact surface 542.

In some embodiments the needle 116, 216, 316, 416, 516, 616, 716 is configured to penetrate the attachment element 221, 321, 421, 521, 621, 721 and/or the adhesive region 223, 323, 423, 523a, 523b, 623, 723 during delivery of medicament from the medicament cartridge 104, 204, 304, 504, 604, 704. This is where the attachment element or adhesive region extends across a path of the needle 116, 216, 316, 416, 516, 616, 716. However it can be envisaged that the attachment element 221, 321, 421, 521, 621, 721 or adhesive regions 223, 323, 423, 523a, 523b, 623, 723 have a portion that is absent where the needle protrudes, or the attachment element 221, 321, 421, 521, 621, 721 or adhesive regions 223, 323, 423, 523a, 523b, 623, 723 are located surrounding or next to the path of the needle 116, 216, 316, 416, 516, 616, 716. The path of the needle is the path the needle 116, 216, 316, 416, 516, 616, 716 takes as it moves from its initial position retracted within the injection device 100, 200, 300, 400, 500, 600, 700, to an extended/activated position for the delivery of medicament, where it extends from a distal most end of the injection device 100, 200, 300, 400, 500, 600, 700.

In some embodiments the medicament delivery device 100, 200, 300, 400, 500, 600, 700 is an auto-injector. In some embodiments the medicament delivery device comprises manual needle insertion, in others the medicament delivery device comprises automatic needle insertion.

In some embodiments automatic needle insertion is triggered by movement of the needle cover 118, 218, 318, 418, 518, 618, 718 towards the main body 102, 202, 302, 303, 402, 502, 602, 702, in other embodiments the medicament delivery device 100, 200, 300, 400, 500, 600, 700 comprises a button or alternative activation means to activate automatic needle insertion.

Although pulling the user's skin taut is described with reference to FIGS. 9A and 9B. It can be envisaged that this is applicable to any embodiment in which the protective barrier 225, 325, 425, 525, 625, 725 is against a user's skin during removal.

The term "protective barrier" as used throughout, may also mean a protective barrier with more than one component, for example, two parts, the description being applicable to both, or all, parts.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g., a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport syndrome.

Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

An example drug delivery device may involve a needle-based injection system as described in Table 1 of section 5.2 of ISO 11608-1:2014(E). As described in ISO 11608-1:2014 (E), needle-based injection systems may be broadly distinguished into multi-dose container systems and single-dose (with partial or full evacuation) container systems. The container may be a replaceable container or an integrated non-replaceable container.

As further described in ISO 11608-1:2014(E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1:2014(E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1:2014 (E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

Those of skill in the art will understand that modifications (additions and/or removals) of various components of the embodiments described herein may be made without departing from the full scope and spirit of the present disclosure, which encompass such modifications and any and all equivalents thereof.

LIST OF REFERENCE NUMBERS

100—injection device
102—outer casing/housing/main body
104—reservoir
106—plunger
108—collar
110—cap
112—longitudinal axis
113—stopper
114—rear casing
116—needle
118—needle shroud/sleeve/cover
120—control spring
122—drive spring
124—injection site
126—distal end
128—proximal end
200—injection device
202—main body
206—plunger
215—needle carrier
216—needle
217—needle cover side walls
218—needle cover
219—needle cover contact face
221—attachment element
223—adhesive region
224—injection site
225—protective barrier
226—distal end
227—outer frame
228—proximal end
229—frame cavity
230—barrier first end
231—outer frame internal wall
232—barrier second end
233—folded portion
234—fold
257—flange
300—injection device
302—main body
315—needle carrier
316—needle
317—needle cover side walls
318—needle cover
319—needle cover contact face
321—attachment element
323—adhesive region
324—injection site
325—protective barrier
326—distal end
327—outer frame
328—proximal end
330—barrier first end
331—outer frame internal wall
332—barrier second end
333—folded portion
334—fold
357—flange
400—injection device
402—main body 415—needle carrier
416—needle
417—needle cover side walls
418—needle cover
419—needle cover contact face
421—attachment element
423—adhesive region
424—injection site
425—protective barrier
426—distal end
427—outer frame
428—proximal end
430—barrier first end
431—outer frame internal wall
432—barrier second end
434—fold
440—attachment element support
500—injection device
502—main body
504—reservoir/container of medicament
506—plunger
515—needle carrier
516—needle
517—needle cover side walls
518—needle cover
519—needle cover contact face
521—attachment element
523a—first adhesive region
523b—second adhesive region
524—injection site
525—protective barrier
526—distal end
527—outer frame
528—proximal end
529—frame cavity
530—barrier first end
531—outer frame internal wall
532—barrier second end
533—folded portion
534—fold
541—outer frame housing
542—contact surface
543—removal arm
544—aperture
545—outer frame surrounding wall
546—needle hole
547—proximal end removal arm
548—distal end removal arm
549—internal face
550—fastener
551—intermediate point
552—front end device
553—rear end device
554—pivotable connection
600—injection device
602—main body
616—needle
617—needle cover side walls
618—needle cover
619—needle cover contact face
621—attachment element
623—adhesive region
624—injection site
625—protective barrier
626—distal end
627—outer frame
628—proximal end
630—barrier first end
632—barrier second end
633—folded portion
634—fold
655—rollers/releasable mechanism
657—flange
700—injection device
702—main body
717—needle cover side walls
718—needle cover
719—needle cover contact face
721—attachment element
723—adhesive region
724—injection site
725—protective barrier
726—distal end
727—outer frame
728—proximal end
730—barrier first end
732—barrier second end
734—fold
756a—first distal tension member/roller
756b—second distal tension member/roller
756c—first proximal tension member/roller
756d—second proximal tension member/roller
801—one step of a method of operating a medicament delivery device
802—one step of a method of operating a medicament delivery device
803—one step of a method of operating a medicament delivery device
804—one step of a method of operating a medicament delivery device

The invention claimed is:

1. A medicament delivery device comprising:
a main body arranged to receive a medicament cartridge;
a needle for delivery of medicament from the medicament cartridge;
a needle cover moveable between an initial position, in which the needle cover covers the needle, and an activated position for dispensing medicament from the medicament delivery device, wherein in the activated position the needle protrudes from a distal end of the needle cover;
an outer frame, moveable relative to the main body between an extended position in which the outer frame extends past a distal end of the needle, and a retracted position in which the outer frame is moved towards the main body; and
an attachment element comprising an adhesive region for attaching the medicament delivery device to a surface when the needle cover is in the activated position, the attachment element comprising a protective barrier covering the adhesive region,
wherein the protective barrier is coupled to the outer frame and is removed from the attachment element to expose the adhesive region as the outer frame is moved towards the retracted position, and
wherein the protective barrier is configured to pull the surface in a direction away from an injection site as the protective barrier is removed from the attachment element.

2. The medicament delivery device according to claim 1, wherein the protective barrier is removed from the attachment element, and the needle cover is moved from the initial position to the activated position, with a single action of providing a force on the medicament delivery device in a distal direction.

3. The medicament delivery device according to claim 1, wherein the protective barrier comprises a folded portion releasably secured to the attachment element.

4. The medicament delivery device according to claim 3, wherein the folded portion comprises a double layer of the protective barrier covering at least a portion of the attachment element.

5. The medicament delivery device according to claim 3, wherein a second end of the protective barrier is releasably secured to the attachment element, and the second end is folded towards the attachment element to form the folded portion.

6. The medicament delivery device according to claim 1, wherein the outer frame is external to the main body in both the extended position and the retracted position.

7. The medicament delivery device according to claim 1, wherein an adhesive force from the attachment element is greater than a spring force of the needle cover.

8. The medicament delivery device according to claim 1, wherein when the needle cover is in the initial position, the attachment element is positioned set back in a proximal direction from a distal most end of the medicament delivery device.

9. The medicament delivery device according to claim 1, wherein the outer frame is pivotable relative to the main body to move between the extended position and the retracted position.

10. The medicament delivery device according to claim 9, wherein the outer frame comprises a removal arm, wherein a first end of the removal arm is pivotally coupled to the main body, and a second end of the removal arm is moveable relative to an internal face of a contact surface of the outer frame.

11. The medicament delivery device according to claim 10, wherein as the outer frame moves from the extended position to the retracted position, the second end of the removal arm is pushed along the internal face of the outer frame to pull the protective barrier away from the attachment element.

12. The medicament delivery device according to claim 9, wherein the protective barrier is configured to be pulled through an aperture in a contact surface of the outer frame.

13. The medicament delivery device according to claim 1, wherein the outer frame comprises a releasable mechanism to automatically retract the protective barrier from the attachment element, wherein the releasable mechanism is activated as the outer frame is moved towards the main body.

14. The medicament delivery device according to claim 13, wherein the releasable mechanism comprises at least one biased roller, and a first end of the protective barrier is wound around the at least one biased roller, and a second end of the protective barrier is releasably attached to the attachment element.

15. The medicament delivery device according to claim 1, wherein the outer frame comprises at least one tension member to hold the protective barrier in tension as it is removed from the attachment element.

16. The medicament delivery device according to claim 1, wherein the protective barrier comprises two components and the surface is pulled in opposing directions by each part of the protective barrier as the protective barrier is removed from the attachment element.

17. The medicament delivery device according to claim 1, wherein the adhesive region holds the surface taut until the medicament delivery device is removed from the surface.

18. The medicament delivery device according to claim 1, comprising a container of medicament.

19. A method of operating a medicament delivery device, the method comprising: moving an outer frame relative to a main body of the medicament delivery device from an extended position, in which the outer frame extends past a distal end of a needle, to a retracted position, in which the outer frame is moved towards the main body; exposing an adhesive region of an attachment element by removing a protective barrier covering the adhesive region, wherein the protective barrier is coupled to the outer frame of the medicament delivery device and is removed as the outer frame is moved towards the retracted position; and adhering the exposed adhesive region of the attachment element to a surface for preparation of delivery of a medicament, wherein the protective barrier is configured to pull the surface in a direction away from an injection site as the protective barrier is removed from the attachment element.

* * * * *